(12) United States Patent
Omer et al.

(10) Patent No.: US 11,638,642 B2
(45) Date of Patent: May 2, 2023

(54) OPHTHALMIC DEVICE HAVING OPAQUE AND DECENTERED LIGHT-TRANSMISSIVE PORTIONS FOR ALLEVIATING SYMPTOMS RELATING TO OCULAR DISEASES

(71) Applicant: MOR RESEARCH APPLICATIONS LTD., Tel Aviv (IL)

(72) Inventors: Gonen Omer, Gedera (IL); Ori Mahler, Tel Aviv (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 16/483,752

(22) PCT Filed: Mar. 1, 2018

(86) PCT No.: PCT/IB2018/051299
§ 371 (c)(1),
(2) Date: Aug. 6, 2019

(87) PCT Pub. No.: WO2018/158715
PCT Pub. Date: Sep. 7, 2018

(65) Prior Publication Data
US 2020/0022805 A1 Jan. 23, 2020

Related U.S. Application Data

(60) Provisional application No. 62/551,817, filed on Aug. 30, 2017.

(51) Int. Cl.
| A61F 2/16 | (2006.01) |
| G02C 7/04 | (2006.01) |
| A61F 2/14 | (2006.01) |

(52) U.S. Cl.
CPC .............. *A61F 2/1613* (2013.01); *A61F 2/14* (2013.01); *A61F 2/15* (2015.04); *G02C 7/048* (2013.01); *A61F 2002/1696* (2015.04); *A61F 2240/002* (2013.01); *G02C 2202/04* (2013.01)

(58) Field of Classification Search
CPC .. A61F 2/1613; A61F 2/15; A61F 2/14; A61F 2002/1696; A61F 2240/002; G02C 2202/04
See application file for complete search history.

(56) References Cited

U.S. PATENT DOCUMENTS

| 3,297,396 A | 1/1967 | Wesley |
| 4,573,774 A | 3/1986 | Sitterle |
| 4,581,031 A | 4/1986 | Koziol et al. |
| 4,955,902 A | 9/1990 | Kelman |

(Continued)

FOREIGN PATENT DOCUMENTS

| CN | 103068340 A | 4/2013 |
| EP | 2301477 A1 | 3/2011 |

(Continued)

*Primary Examiner* — Javier G Blanco
(74) *Attorney, Agent, or Firm* — Soroker Agmon Nordman

(57) ABSTRACT

Embodiments concern an intraocular implantable device operable comprising a disk-shaped body having a symmetry axis and which further comprises a light-transmissive portion and an opaque portion wherein the light-transmissive portion is decentered with respect to the symmetry axis.

6 Claims, 10 Drawing Sheets

(56) References Cited

U.S. PATENT DOCUMENTS

| | | | |
|---|---|---|---|
| 5,434,630 A * | 7/1995 | Bransome | G02C 7/16 |
| | | | 351/159.02 |
| 5,719,656 A | 2/1998 | Bowling | |
| 6,062,687 A | 5/2000 | Lofgren-Nisser | |
| 6,139,145 A | 10/2000 | Israel | |
| 6,197,057 B1 | 3/2001 | Peyman et al. | |
| 8,308,292 B2 * | 11/2012 | Arai | G02C 7/049 |
| | | | 351/159.24 |
| 2002/0019667 A1 | 2/2002 | Baikoff | |
| 2002/0052652 A1 | 5/2002 | Schachar | |
| 2004/0082995 A1 | 4/2004 | Woods | |
| 2004/0117013 A1 | 6/2004 | Schachar | |
| 2004/0233383 A1 * | 11/2004 | Sandler | A61F 2/14 |
| | | | 351/159.6 |
| 2006/0187409 A1 | 8/2006 | Hull | |
| 2006/0235514 A1 * | 10/2006 | Silvestrini | C08L 27/16 |
| | | | 351/159.6 |
| 2009/0204207 A1 | 8/2009 | Blum | |
| 2010/0265458 A1 | 10/2010 | Nachev et al. | |
| 2011/0040376 A1 * | 2/2011 | Christie | B29D 11/00317 |
| | | | 623/6.17 |
| 2011/0153014 A1 | 6/2011 | Zhang et al. | |
| 2012/0136438 A1 | 5/2012 | Moriarty | |
| 2013/0211515 A1 | 8/2013 | Blum et al. | |
| 2016/0193039 A1 | 7/2016 | Qureshi et al. | |

FOREIGN PATENT DOCUMENTS

| | | |
|---|---|---|
| GB | 1276003 A | 6/1972 |
| GB | 2458495 | 9/2009 |
| GB | 2458495 A | 9/2009 |
| WO | 93/08784 A1 | 5/1993 |
| WO | WO 2015006839 A1 | 1/2015 |
| WO | WO 2015022515 A1 | 2/2015 |
| WO | WO 2017149470 A1 | 9/2017 |

* cited by examiner

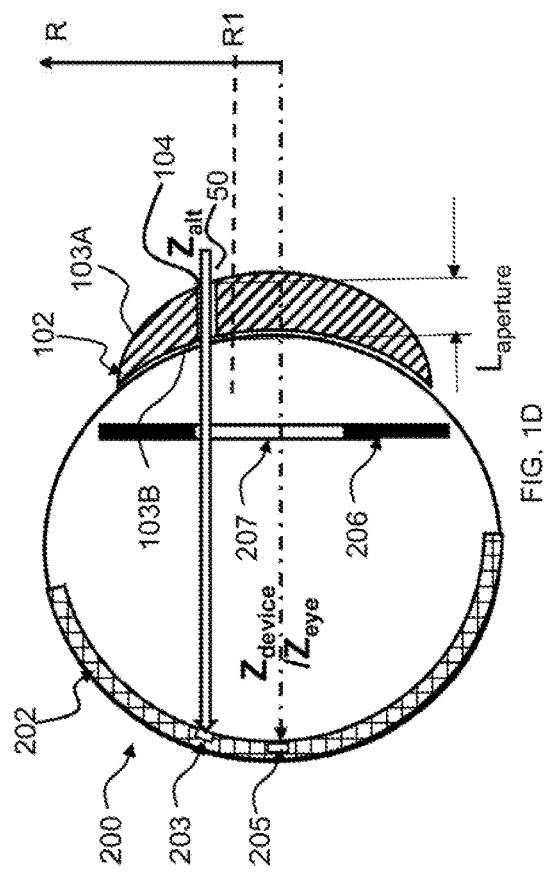
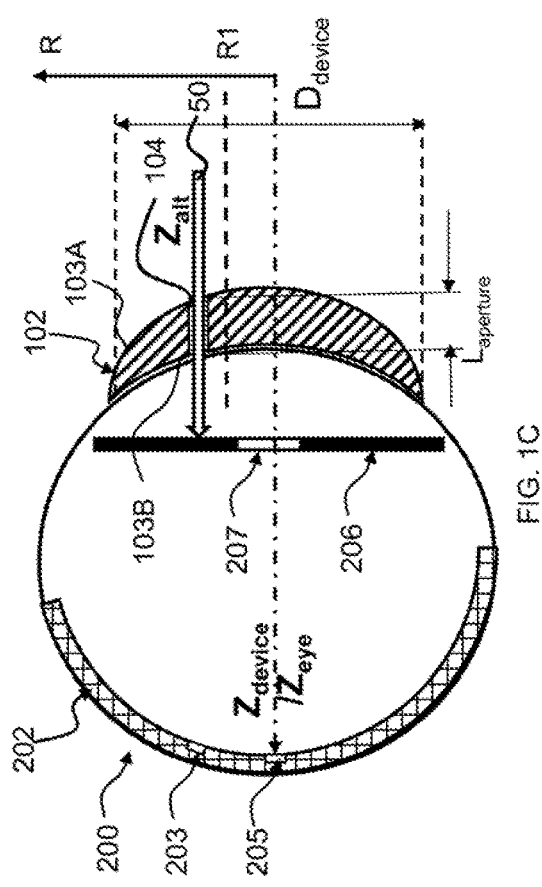

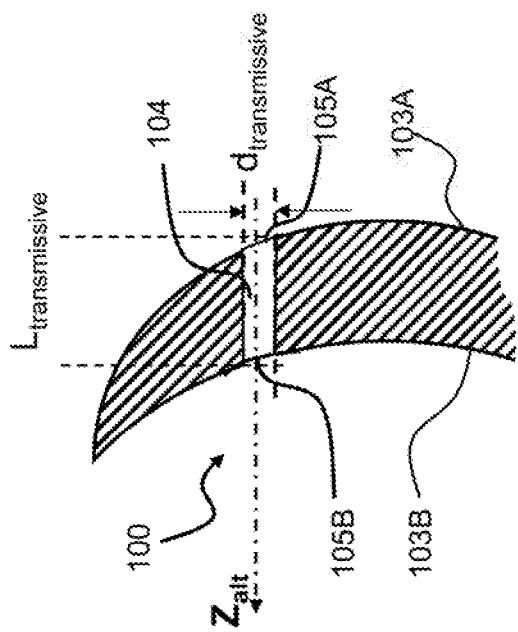
FIG. 2B
FIG. 2A

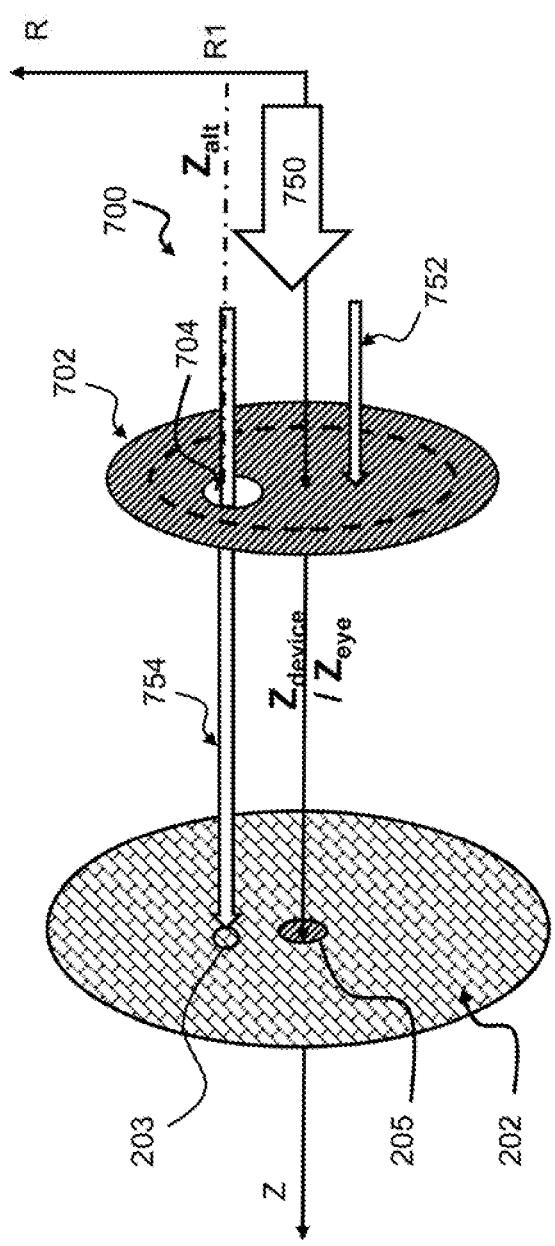
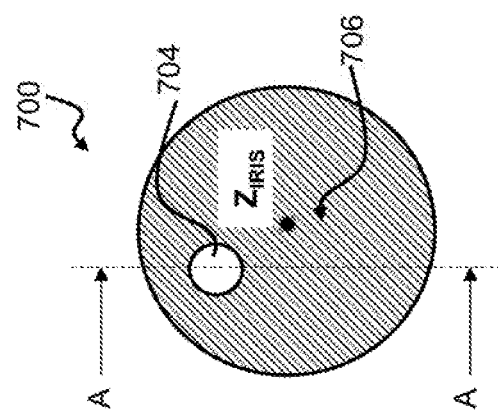
FIG. 7A
FIG. 7B

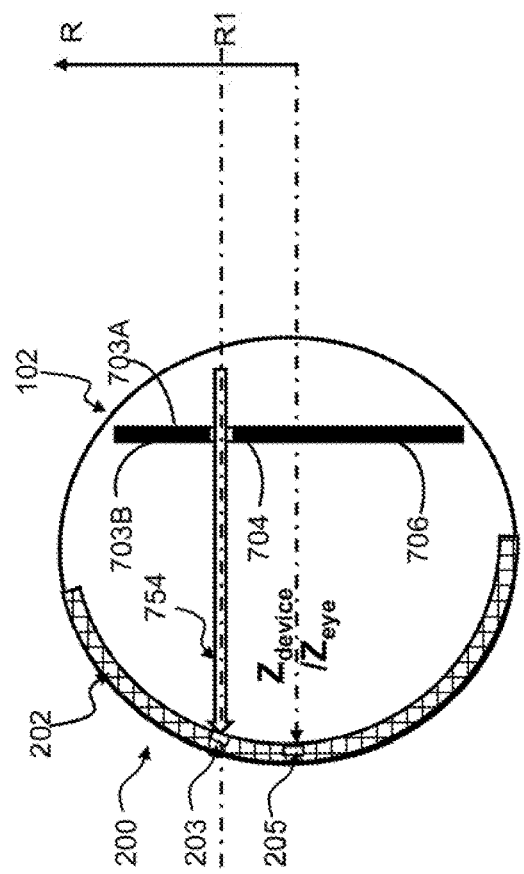
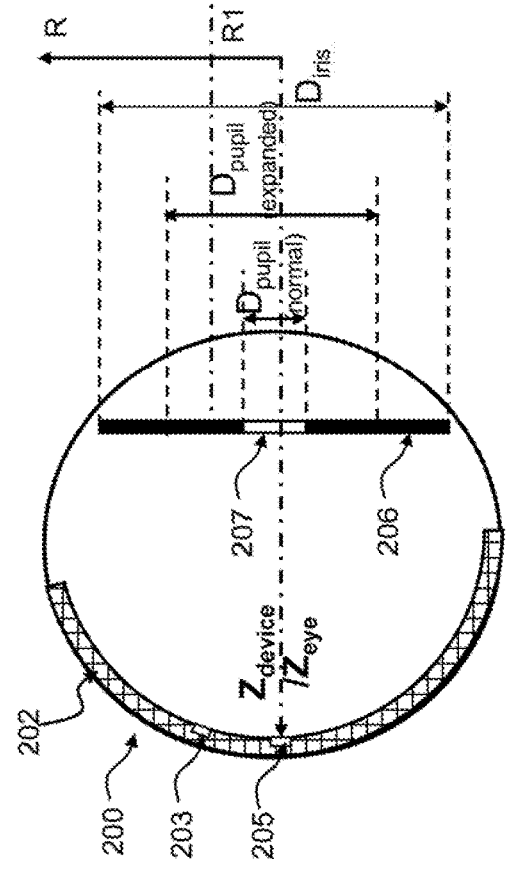

OPHTHALMIC DEVICE HAVING OPAQUE AND DECENTERED LIGHT-TRANSMISSIVE PORTIONS FOR ALLEVIATING SYMPTOMS RELATING TO OCULAR DISEASES

BACKGROUND

The Macula describes an area on the retina of the human eye which is responsible for sharp central vision due to the comparatively high receptor density. Age-related Macular Degeneration, also known as AMD, degenerates macular tissue and thus reduces the density of receptors, causing severe disruption of vision acuity in patients. Therefore, patients suffering from AMD often heavily rely on peripheral vision for daily tasks. However, the peripheral retina has low receptors densities relative to the macula, which leads to a lower resolution ability.

The fovea is a localized region of the macula with the highest visual acuity, close to the optic axis of the eye, where the inner layers of the retina are absent. Macular degeneration is most debilitating when it disrupts the fovea.

Related art documents include:
[1] U.S. Pat. No. 4,955,902A
[2] US20020196 7A
[3] US2012136438A
[4] US2013211515A
[5] US2016193039A
[6] WO15006839A1
[7] US2004117013A
[8] U.S. Pat. No. 6197057B
[9] U.S. Pat. No. 4,581,031A
[10] US2006187409A
[11] US2010265458A
[12] U.S. Pat. No. 6,139,145A
[13] US2004082995A
[14] U52002052652A
[15] US2011153014A Acknowledgement of the above related art documents is not to be inferred as meaning that these are in any way relevant to the patentability of the presently disclosed subject matter.

The description above is presented as a general overview of related art in this field and should not be construed as an admission that any of the information it contains constitutes prior art against the present patent application.

OVERVIEW

Example 1 includes an optical eye-contact device comprising a contact lens body having a rotational symmetry axis, the contact lens body comprising a light-transmissive portion and a distal and proximal device surface; and an opaque portion which is non-transmissive to visible light, wherein the light-transmissive portion is decentered with respect to the contact lens body's symmetry axis and allows a portion of light incident on the distal surface to propagate from the distal device surface via the light-transmissive portion and emanate from the proximal device surface.

Example 2 includes the subject matter of example 1 and, optionally, wherein when the contact lens body operably engages an eye of a patient, the symmetry axis of the eye-contact device coincides with the eye's optical axis, Example 3 includes the subject matter of example 2 and, optionally, wherein the contact lens body comprising the light-transmissive portion is configured such that light propagating through the light-transmissive portion is incident onto the patient's macula but not on the fovea located in the macula.

Example 4 includes the subject matter of example 2 and, optionally, wherein the contact lens body which comprises the light-transmissive portion is configured so that light propagating through the light-transmissive portion is incident onto on an area of the patient's retina that is outside the macula.

Example 5 includes the subject matter of any one of the examples 1 to 4 and, optionally, wherein the contact lens body is configured to at least partially or fully compensate for refractive errors of the patient's eye.

Example 6 includes the subject matter of example 5 and, optionally, wherein the light-transmissive portion has a concave or convex shape.

Example 7 includes the subject matter of example 5 or 6 and, optionally, wherein the contact lens body is configured to at least partially compensate for myopia of the patient.

Example 8 includes the subject matter of any one of the examples 1 to 7 and, optionally, wherein the light-transmissive portion comprises solid or gel-based material.

Example 9 includes the subject matter of any one of the examples 1 to 8 and, optionally, wherein the light-transmissive portion comprises fluid material.

Example 10 includes the subject matter of example 9 and, optionally, wherein the fluid material comprises air, gas and/or liquid material.

Example 11 includes the subject matter of any one of the examples 1 to 4 and, optionally, wherein the light-transmissive portion is a physical through-hole that extends from the distal to the proximal device surface.

Example 12 concerns an ophthalmic trial kit comprising a plurality of trial eye-contact devices each having different values relating to optical design parameters of the trial eye-contact devices such to allow a user of the trial kit to sequentially select at least two of the plurality of trial eye-contact devices for implementing an iterative optimization process in which the parameter values are convergent until for the given plurality of trial eye-contact devices, a combination of device parameters is determined that is considered optimal for the given patient.

Example 13 concerns a method for manufacturing an optical eye-contact device, the method comprising receiving information pertaining to a condition of a patient's eye; and providing, based on the received information, an optical eye contact device.

Example 14 concerns an implantable ophthalmic device, comprising a substantially circular-shaped body having a distal device surface and a proximal device surface and comprising a light-transmissive portion; and an opaque portion; wherein the light-transmissive portion is decentered with respect to the symmetry axis of the substantially circular-shaped body and operable to direct light from the distal device surface to the proximal device surface. The circular-shaped body may for example exhibit an about elliptical geometry when viewed from the side as for a lens, or an about rectangular and flat geometry having about parallel proximal and distal surfaces when viewed from the side as for a disk.

Example 15 includes the subject matter of example 14 and, optionally, wherein the substantially circular-shaped body is disk- or lens-shaped and configured to be respectively employable as an implantable artificial iris or an implantable intraocular lens, wherein the light-transmissive portion is configured to direct light propagating through the light-transmissive portion such to be incident onto the eye's macula but not on the fovea located in the macula.

Example 16 includes the subject matter of examples 14 or 15, wherein the light-transmissive portion is configured such that that light propagating through the light-transmissive portion is incident onto on an area of the patient's retina that is outside the macula.

Example 17 includes the subject matter of any one of the examples 14 to 16, wherein the light-transmissive portion is a physical through-hole that extends from the distal to the proximal device surface.

Example 18 includes the subject matter of any one of the examples 14 to 17 and, optionally, wherein the light-transmissive portion has an optical axis that coincides with a patient's iris if such iris was present and in the non-expanded state.

Example 19 concerns a method for manufacturing an implantable ophthalmic device according to any one of the examples 14 to 18, the method comprising: receiving information pertaining to a condition of a patient's eye; and providing, based on the received information, an optical eye-contact device.

Example 20 concerns a trial kit comprising a plurality of trial eye-contact devices each having different values relating to optical design parameters of the trial eye-contact devices such to allow a user of the trial kit to sequentially select at least two of the plurality of trial eye-contact devices for implementing an iterative optimization process in which values pertaining to the optical design parameters are convergent until for a given plurality of trial eye-contact devices, a combination of device parameters is determined that is considered optimal for a given patient for providing an implantable ophthalmic device according to any one of the example 14 to 18.

This overview introduces a selection of concepts in a simplified form that are further described below in the Description of the Figures and the Detailed Description. This Overview is not intended to identify key features or essential features of the claimed subject matter, nor is it intended to be used to limit the scope of the claimed subject matter

BRIEF DESCRIPTION OF THE FIGURES

The figures illustrate generally, by way of example, but not by way of limitation, various embodiments discussed in the present document.

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. References to previously presented elements are implied without necessarily further citing the drawing or description in which they appear. The number of elements shown in the Figures should by no means be construed as limiting and is for illustrative purposes only. The figures are listed below

FIG. 1C is a schematic cross-sectional side view illustration of the eye-contact device in operable engagement with the patient's eye before expansion of the eye's pupil, according to some embodiments;

FIG. 1D is a schematic cross-sectional side view illustration of the eye-contact device in operable engagement with the patient's eye after expansion of the eye's pupil, according to some embodiments;

FIG. 2A is a schematic partial cross-sectional view of the eye-contact device of FIG. 1B;

FIG. 2B is a schematic side-view illustration of an eye-contact device, according to some other embodiments;

FIGS. 5A and 5B are schematic illustrations of an ophthalmic trial kit, according to some embodiments;

FIG. 7A is a schematic isometric side view illustration of an artificial iris in operable position within a patient's eye, according to some embodiments;

FIG. 7B a schematic front view illustration of the artificial iris, according to some embodiments;

FIG. 7C is a schematic cross-sectional side view illustration of a patient's iris in a normal "non-expanded" state, according to some embodiments; and FIG. 7D is a schematic cross-sectional side view, illustration of the implantable artificial iris after being implanted into a patient's eye, according to some embodiments.

DETAILED DESCRIPTION

Figure 1A:
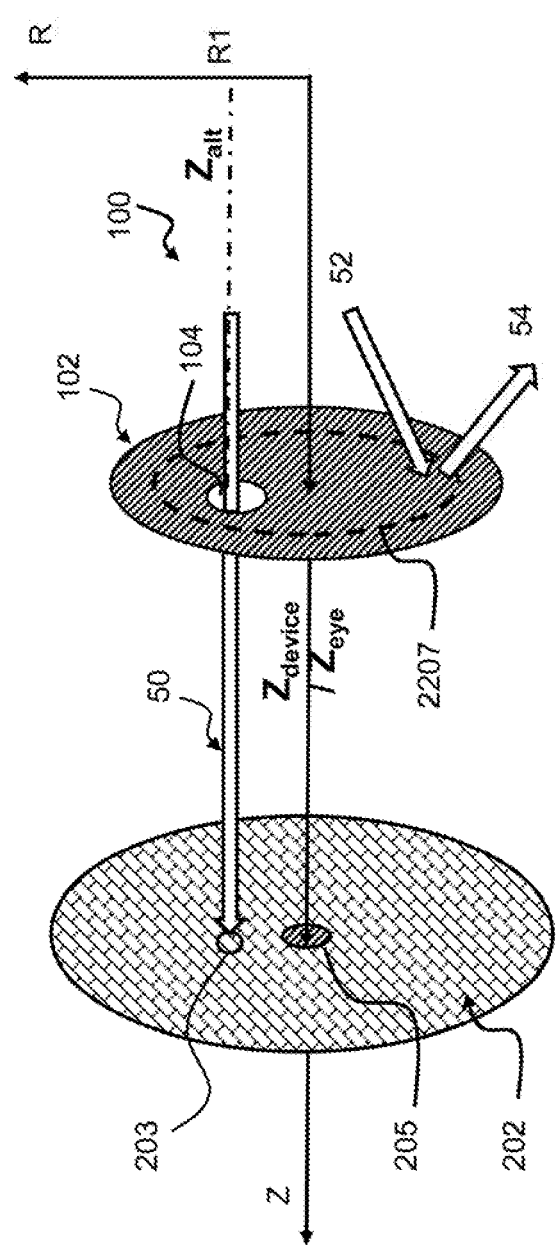
FIG. 1A is a schematic isometric side view illustration of an eye-contact device in operable engagement with a patient's eye, according to some embodiments.
Figure 1B:
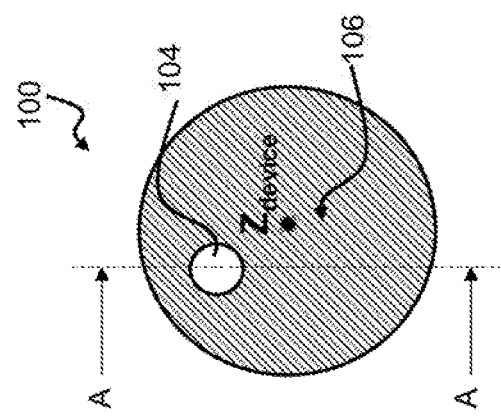
FIG. 1B is a schematic front view illustration of the eye-contact device, according to some embodiments.

Aspects of embodiments of disclosed herein relate to devices and methods for alleviating complications caused by age-related macular degeneration (AMD) and/or other ophthalmic (including, e.g., neuro-ophthalmic) conditions or diseases of a patient. Accordingly, while certain embodiments may herein be described with respect to AMD, this should by no means be construed in a limiting manner.

The following description of devices, kits and methods for alleviating ophthalmic conditions is given with reference to particular examples, with the understanding that such devices, kits and methods are not limited to these examples. It should be noted that the terms "device", "eye-contact device", "external eye-contact device", "optical eye-contact device" and "definite eye-contact device" may herein be used interchangeably. It is noted that the term "definite eye-contact device" may herein be used in some instances to distinguish it from "trial eye-contact devices" which may be employed, e.g., as part of a trial method or method for obtaining information pertaining to the (e.g., clinical) condition of a patient's eye, to determine the values relating to device design and/or manufacturing parameters (e.g., optical parameters and/or design parameters) suitable for a given patient for the manufacturing of a "definite" eye-contact device that is custom fitted to the given patient according to the determined values.

Reference is made to FIGS. 1A to 1D. An optical eye-contact device 100 (also: external contact lens) comprises according to some embodiments a contact lens body 102 which may have a spherical shape and, e.g., cover a surface area which may be smaller than that of a hemisphere. The term "spherical" as used herein may also encompass the meaning of the term "substantially spherical".

Contact lens body 102 may have a distal or outer (e.g., at least partially convex) device surface 103A which, when contact lens body 102 is operably engaged with a patient's eye 200, may be exposed directly to ambient light, and a proximal or inner (e.g., at least partially concave) device surface 103B adapted or configured to allow contact lens body 102 to operably engage with the anterior surface of the patient's eye 200. It is noted that the eye-contact device may be considered to be an "external eye-contact device" to exclude intra-ocular implants. Eye-contact device 100 may be exchangeable by the patient himself manually like regular contact lenses, e.g., as known in the art, without requiring the assistance of professional medical staff.

Contact lens body 102 may have a rotational symmetry axis or symmetry of revolution around axis $Z_{device}$. In an embodiment, contact lens body 102 comprises a light-transmissive portion (also: area) 104 and an opaque portion or area 106 that is non-transmissive to visible light. Optionally, light-transmissive portion 104 and opaque portion 106 complement each other to form contact lens body 102. Light-transmissive portion 104 allows the transmission of light from distal device surface 103A to proximal device surface 103B of eye-contact device 100. In one embodiment, opaque portion 106 is non-transmissive to visible light or, otherwise stated, fully opaque to visible light 50.

Light-transmissive portion 104 is located off-center, off-axis or decentered with respect to the contact lens body's symmetry axis $Z_{device}$ by a radius R1.

Except for decentered light-transmissive portion 104, contact lens body 102 may be opaque to visible light. Accordingly, as schematically shown in FIG. 1A, light 52 that is incident onto opaque portion 106 may be absorbed by and/or reflected from opaque portion 106. Light reflected from opaque area is herein referenced by alphanumeric designation "54".

Further reference is made to FIG. 2A. FIG. 2A schematically shows a partial cross-sectional view of eye-contact device 100 along virtual surface A-A schematically shown in FIG. 1B. Light-transmissive portion 104 of contact lens body 102 may extend over a length $L_{transmissive}$ from a distal end 105A to a proximal end 105B. The terms "proximal" and "distal" as, used herein refer to positions relative to eye 200 during normal use of eye-contact device 100. In some embodiments, distal end 105A and/or proximal end 105B may be defined by respective distal and/or proximal surfaces.

Optionally, eye-contact device 100 may be configured such that when it is operably engaged with eye 200, the contact lens body's symmetry axis $Z_{device}$ may coincide with the patient's normal optical axis $Z_{eye}$. The term "coincide" as used herein may also encompass the meaning of the term "substantially coincide".

Distal device surface 103A may comprise distal end 105A, and proximal device surface 103B may comprise proximal end 105B of light-transmissive portion 104. Light-transmissive portion 104 allows propagation of light 50 incident onto distal device surface 103A to propagate over the distance D and further via proximal device surface 103B, towards retina 202 of the patient's eye 200.

Light-transmissive portion 104 may define an alternative optical axis $Z_{alt}$. Optionally, alternative optical axis $Z_{alt}$ may run parallel to the contact lens body's symmetry axis $Z_{device}$. Optionally, alternative optical axis $Z_{alt}$ may form an angle with respect to the contact lens body's symmetry axis $Z_{device}$. Optionally, alternatively optical axis $Z_{alt}$ may run partially parallel and partially angled with respect to the contact lens body's symmetry axis $Z_{device}$.

It is noted that the direction of incoming light 50 as shown in the accompanying figures should not be construed in a limiting manner and is for illustrative purposes. Accordingly, light 50 may enter light-transmissive portion 104 from a variety of angles relative to $Z_{alt}$.

In some embodiments, when eye-contact device 100 is set in operable position, alternative optical axis $Z_{alt}$ may run parallel to the optical axis of eye 200 ($Z_{eye}$). In some embodiments, when eye-contact device is set in its operable position, alternative optical axis $Z_{alt}$ may form an angle with respect to the optical axis of eye 200 ($Z_{eye}$).

In some embodiments, when eye-contact device is set in operable position, an angle formed between the alternative optical axis $Z_{alt}$ and the optical axis of eye 200 and/or of the symmetry axis $Z_{device}$ may be such so that the axes are convergent towards the patient's retina 202. In some embodiments, when eye-contact device is set in operable position, an angle formed between the alternative optical axis $Z_{alt}$ and the optical axis of eye 200 and/or of the symmetry axis $Z_{device}$ may be such so that the axes are divergent towards the patient's retina 202.

In some embodiments, the boundaries (e.g., inner walls) of light-transmissive portion 104 may be formed to be convergent towards retina 202 when eye-contact device 100 is set in operable position. In some embodiments, the boundaries (e.g., inner walls) of light-transmissive portion 104 may be formed to be divergent towards retina 202 when eye-contact device 100 is set in operable position.

Radius R1 between $Z_{device}$ and $Z_{alt}$ may for example range from 1.5 mm to 3 mm. As shown schematically in FIG. 2A, light-transmissive portion 104 may have a lateral extension $d_{transmissive}$ (e.g., diameter in case of a substantially circular cross-sectional geometry) ranging, for example, from 0.3 mm to 5 mm. Optionally, light-transmissive portion 104 may comprise or be made of multiple "small" light-transmissive portions (not shown).

In some embodiments, it may be required to expand iris 206 of eye 200 to widen pupil 207 for allowing the propagation of light 50 via light-transmissive portion 104 via pupil 207 without hitting or being obstructed by iris 206. FIG. 1C schematically shows iris 206 before expansion, in the narrow state, so that light 50 entering eye 200 through or via light-transmissive portion 104 is incident onto iris 206. FIG. 10 schematically shows iris 206 after its expansion (i.e., in the expanded state) so that light 50 entering eye 200 through or via light-transmissive portion 104 can propagate via pupil 207 towards retina 202. Pupil 207 may be expanded to attain a diameter of at least 6 mm, at least 7 mm, at least 8 mm, or at least 9 mm. Expansion of pupil 207 may for example be imparted onto iris 206 from an initial pupil diameter of 2-4 mm. Broken circular line 2207 in FIG. 1A schematically shows the boundary of pupil 207 relative to eye-contact device 100 when in operable position and when patient's pupil(s) 207 is/are dilated or otherwise set from a "non-expanded state" into an "expanded state". A non-expanded state may refer to a state of an iris 206 and corresponding size of pupil 207 under normal or "good" lighting conditions, excluding, for example, night or other low-light visibility conditions naturally causing the expansion of the pupil. The term "expanded state" as used herein refers to a state in which the pupil is expanded as a result of selectively applying extrinsic means such as composition of matter and/or mechanical assemblies. For instance, expansion of iris 206 may be accomplished in a number of ways including, for example, by applying pupil-dilating eye-drops to eye 200. Non-limiting examples of pupil dilating eyedrops include, for example, Tropicamide and Atropine. Tropicamide may be employed when it is desired to effect pupil dilation for a time period of about 3-4 hours, and Atropine may be employed when it is desired to effect pupil dilation for a time period for 10-14 days. In some embodiments, pupil 207 may be expanded in a surgical manner. In some embodiments, expansion of iris 206 may be achieved by operably engaging an implantable pupil expander (not shown) with iris 206 or by otherwise fixating the iris, at least temporarily, in the expanded state. In some embodiments fasteners such as sutures may be employed, a Light-transmissive portion 104 may be positioned relative to or at a distance from the contact lens' symmetry axis $Z_{device}$ and at an orientation relative to the patients' retina 202, such that at least some of light 50 propagating through light-transmissive portion 104 is incident onto a new main vision spot 203 of the patient's retina 202 which is not yet or only partially damaged due to AMD and/or other ophthalmic diseases. Optionally, light 50 propagating through light-transmissive portion 104 may be focused onto new main vision spot 203. New main vision spot 203 may refer to a vision area of retina 202 having a radius ranging (optionally taking into account the retina's curvature), e.g., from 0.5 mm to 5.5 mm, for the radius of new main vision spot 203. Eye-contact device 100 is configured and operable such that when it is operably engaged with the patient's eye 200, light 50 incident onto eye-contact device 50 is directed onto new main vision spot 203, which is displaced or shifted with respect to a spot of the patient's retina 202 onto which light may normally be focused, which may herein be referred to as "old main vision spot". More specifically, light-transmissive portion 104 directs light 50 onto new main vision spot 203, while at the same time, opaque portion 106 prevents light from entering eye 200. It is noted that the expression "normally" be focused is not limited to a "naked human eye", but may also encompass instances in which a person is wearing prescription spectacles, having a corrective intra-ocular lens and/or the like, e.g., to correct for refractive errors of eye 200.

The patient's macula 205, which includes the fovea not shown), may be considered to be the "old main vision spot". Optionally, new main vision spot 203 may be within the area generally considered to be macula 205. Optionally, new main vision spot 203 may be within the area considered to macula 205, but not on the fovea located in macula 205. Optionally, new main vision spot 203 may be outside the area generally considered to be macula 205. Merely to simplify the discussion herein, and without be construed as limiting, embodiments and/or figures disclosed herein may refer to configurations of eye-contact device 100 where light 50 is incident onto an area of retina 202 that is outside macula 205. Optionally, new main vision spot 203 may become an "old" main vision spot, if retina 202 of the new main vision spot 203 becomes damaged such that another "new" main vision spot 203 has to be localized and/or identified.

Causing light 50 to be incident onto new main vision spot 203 may improve acuity of patients suffering for instance of AMD or other diseases, e.g., from a category that may be considered "legally blind" to above the said category, e.g., "functional". Exemplarily, acuity of vision for the respective eye may be increased from 1/60 or 6/60, to 6/24, 6/30, 6/15, or to 6/12. Exemplarily, acuity of vision for the respective can be increased by at least 10%, 20%, 30%, 40%, 50%, 60%, 70%, 80%, 90%, 100%, 110%, by at least 120%,, by at least 130%, by at least 140%, by at least 150%, by at least 160%, by at least 170%, by at least 180%, by at least 190%, by at least 200%, or by at least 250%, e.g., with respect to a visual acuity determined, e.g., by an eye chart, prior to employing eye-contact device 100. In some embodiments, optical eye-contact device 100 may be operative so that, when in operable position, light is focused onto new main vision spot 203.

In some embodiments, light-transmissive portion 104 may be implemented by a fluid-sealed aperture (also: a physical hole or a pinhole) formed in contact lens body 102. In some embodiments, light-transmissive portion 104 may be a physical through-hole extending from distal device surface 103A to proximal device surface 103B. Otherwise stated, opaque portion 106 may form a through-hole 104 in eye-contact lens body 110.

Generally, a light-transmissive portion may be sufficiently large such that diffraction effects are comparatively insignificant, and yet the light-transmissive portion ma be sufficiently small such to obtain a desired visual acuity.

In some embodiments, light-transmissive portion 104 may be a fluid-filled (e.g., air-filled, gas-filled, or liquid-filled) cavity that is, for example, enclosed by the material of contact lens body 102 and by distal and proximal ends 105A and 105B, respectively. In some other embodiments, light-transmissive portion 104 of contact lens body 102 may comprise solid or gel-based material that is transparent to visible light. It is noted that the term "transparent" may also encompass the meaning of the term "substantially transparent". In some embodiments, light-transmissive portion 104 may be configured to at least partially correct or at least partially compensate for optical (e.g., refractive) error(s) of eye 200, including for example, to compensate for myopia, hyperopia and/or astigmatism of eye 200. In some embodiments, light-transmissive portion 104 may be configured to fully compensate for optical errors of eye 200.

Light-transmissive portion 104 may be flush with opaque portion 106 on either side of optical eye-contact device 100. Contact lens body 102 may be custom fitted to the shape of the patient's cornea 208. Contact lens body 102 may comprise or be made of any suitable material including, for example, Rigid gas-permeable (RGP) material such as, for example, fluorosilicone acrylate, or malleable plastic polymers. In some embodiments, contact lens body 102 may have a "scleral" lens body and therefore be configured to cover most of a patient's sclera 212. In some embodiments, contact lens body 102 may be colored to mimic the natural look of an eye. In some embodiments, optical eye-contact device 100 may be configured such to have therapeutic, sensing, monitoring, detection, and/or recording capabilities.

In one embodiment, contact lens body 102 may be sized (e.g. have a diameter $D_{device}$) such to be partially covered by the eyelids (not shown) when they are open. In another embodiment, contact lens body 102 may be sized to not be covered by the eyelids (not shown) when they are open. Contact lens body 102 may be configured to cover the cornea 208 in its entirety. Contact lens body 102 may, be configured to cover cornea 208 in its entirety and 50% or less of the patient's sclera 212.

Location of new main vision spot 203 may refer to the position of an area on retina 202 at which for a given patient, maximal visual acuity is obtained. It follows from the aforesaid that the location of new main vision spot 203 on retina 202 may differ between patients. Accordingly, radius R1, lateral dimension $d_{transmissive}$, and/or length $L_{transmissive}$ and/or values of additional parameters may be customized to each patient. Optionally, device diameter $D_{device}$, shape of distal device surface 103A and of proximal device surface 103B may be customized for each patient.

The expression "maximal visual acuity" as used herein may optionally refer to a visual acuity that is approximately "maximal" within a certain range for a given patient. Optionally, visual acuity a given patient's sensory vision threshold may be determined using an eye chart (e.g., Early Treatment Diabetic Retinopathy Study (ETDRS) chart, Snellen chart, LogMar chart, E-chart, Amsler Grid, The Bailey-Louie Acuity Chart, etc.).

It is noted that a theoretical maximum, obtainable visual acuity for a given patient may not be accurately determinable as it may depend on many factors which are not accurately measurable and/or controllable including, for example, environmental factors, on the testing procedures performed, sensitivity of the interpretative faculty of the brain, the resolution and/or type of the eye chart employed, and/or accuracy of the instruments used in the testing procedure.

In some embodiments, optical eye-contact device 100 may have a stabilized design to achieve rotational and translational stability when optical eye-contact device 100 is set in operable position. In other words, optical eye-contact device 100 may be configured to remain rotationally and translationally stationary with respect to the eye's optical axis Z when set in operable position.

A stabilized design may be achieved, for example, by designing a bottom portion of optical eye-contact device 100 to be thicker than an upper portion, also known as "prism balance". By thickening the lower portion of the contact lens, the upper eyelid can slide over the comparatively thin superior portion during blinking, thus forcing the thicker inferior portion down. In this way, optical eye-contact device 100 may maintain a desired orientation. Optionally, optical eye-contact device 100 may have a mass distribution configured to maintain rotational stability due to gravitation.

The shape of distal device surface 103A and of proximal device surface 103B shown in the accompanying figures are for illustrative purposes and should by no means be construed in a limiting manner. FIG. 2B schematically shows another example of a shape of optical eye-contact device 100.

Figure 3B:
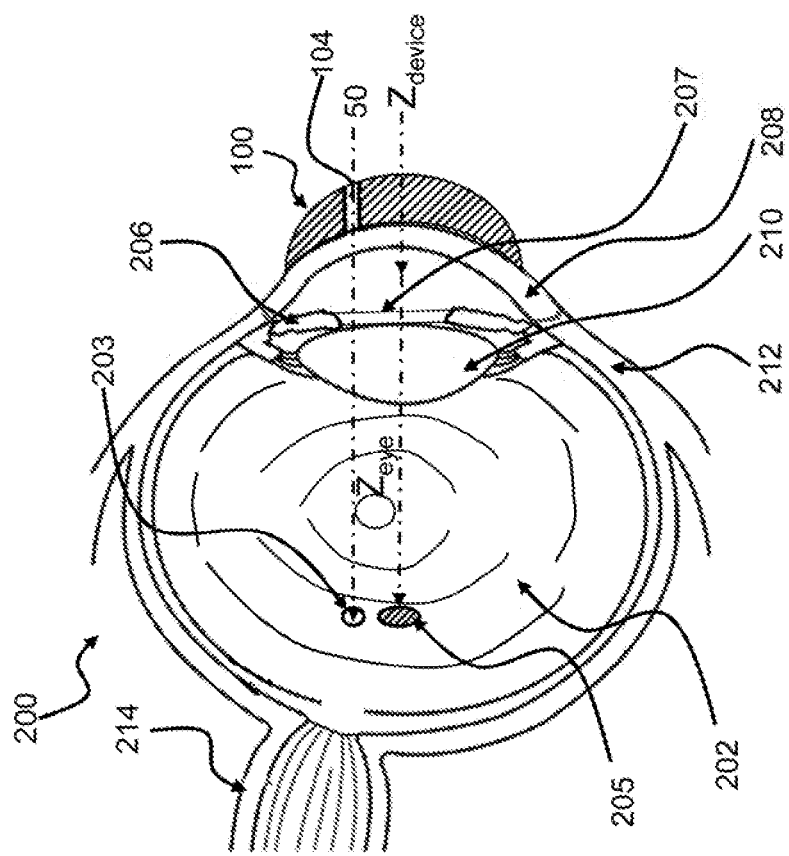
FIG. 3B is a schematic and more detailed side view illustration of the eye-contact device in operable engagement with a patient's eye after expansion of the eye's pupil, according to some embodiments.
Figure 3A:
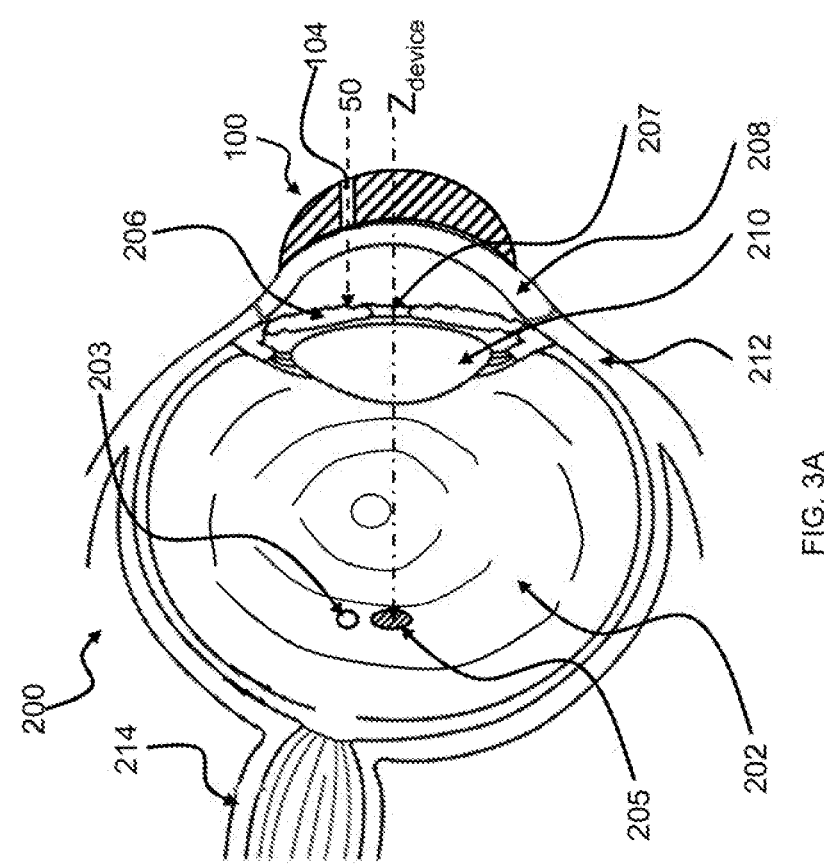
FIG. 3A is a schematic and more detailed side view illustration of the eye-contact device in operable engagement with a patient's eye before expansion of the eye's pupil, according to some embodiments.

Additional reference is made to FIGS. 3A and 3B. As schematically shown in FIGS. 3A and 3B, light 50 incident onto distal end 105A propagates through light-transmissive portion 104 over a distance $L_{transmissive}$ and exits from proximal end 105B from where light 50 may further propagate through the cornea 208 of eye 200. In FIG. 3A, pupil 207 formed by iris 206 is shown in a non-retracted (e.g., non-dilated) state such that light 50 is incident onto iris 206, thereby possibly preventing light 50 from propagating towards retina 202.

FIG. 3B schematically shows pupil 207 of eye 200 in an expanded state (e.g., through dilation). When pupil 207 is in the expanded state, light 50 propagating through cornea 208 of eye 200 may pass through pupil 207 and further propagate through the eye's lens 210 via the vitreous body (not shown) until incident onto new main vision spot 203.

To simplify the discussion herein, optical refraction and/or diffraction and/or other optical phenomenon relating to light 50 propagating from distal end 105A of light-transmissive portion 104 until light 50 is incident onto new main vision spot 203 of retina 202 may herein be neglected.

As already indicated herein, new main vision spot 203 is shifted with respect to, an old, vision spot (e.g., temporally, nasally shifted, upwards or downwards in eye 200), which may be macula 205. The length the curvature between the center of macula 205 and the center of new main vision spot 203 may be in the range, for example, from 0.5 mm to 3 mm. Light 50 incident onto photo-receptors (not shown) located in new main vision spot 203 may cause the generation of signals which are transmitted to the patient's brain (not shown) via optic nerve 214.

Figure 4:
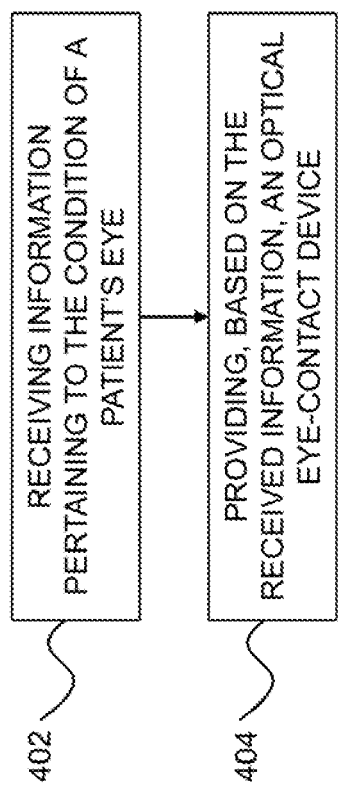
FIG. 4 is a flow chart of a method for manufacturing an eye-contact device, according to some embodiments.

Additional reference is made to FIG. 4. A method for manufacturing optical eye-contact device 100 may include, for example, receiving information pertaining to the (e.g., clinical) condition of a patient's eye including, for example, the condition of the patient's retina 202 (step 402). In case the patient's visual acuity is adversely affected, e.g., due to AMD, the information may relate to or be descriptive of the location where the patient's retina 202 is comparatively intact. The location information may for example be indicative of R1 that is optimal for the given patient and further indicative of the rotational (also: angular) position of light-transmissive portion 104 (e.g., in terms of clockwise angular progression).

The method may further include providing, based on the received information, optical eye-contact device 100 (step 404). More specifically, the optical eye-contact device 100 may be provided such that the device's operative parameters are adjusted to the received information pertaining to the clinical condition of the patient's eye. Providing-eye contact device 100 may thus be customized to a given patient's specific needs.

Optical eye-contact device 100 may be provided using various manufacturing techniques that are based on, for example, printing technologies, lathe forming, 3-D contouring, injection molding and/or any other suitable manufacturing techniques.

Information pertaining to the clinical condition of a patient's eye may be obtained in various manners. For example, the clinical condition of a retina 202 for instance may be determined by employing various imaging techniques such as, e.g., Optical Coherence Tomography (OCT), Fundus Photography and/or Angiography.

In some embodiments, eye-contact devices 100 may be operable to allow at least partial correction of refractive errors. For instance, light-transmissive portion 104 may be shaped to at least partially correct for refractive vision errors. For instance, light-transmissive portion 104 may be configured (e.g., shaped) to correct for myopia, hyperopia and/or astigmatism. Optionally, the surfaces of distal end 105A and of proximal end 105B of light-transmissive portion 104 may be shaped in a concave (e.g., biconcave) or convex (e.g., biconvex) manner with respect to each other.

Further reference is made to FIG. 5. Aspects of embodiments relate to a trial set (also: ophthalmic) trial kit or kit) 500 comprising a plurality of trial eye-contact devices, herein respectively referenced by alphanumeric designations "510-1" to "510-$n$". Each one of the trial-contact devices 510-1 to 510-$n$ may possess different design parameter values. Trial kit 500 may be configured to allow a user thereof (e.g., an ophthalmologist and/or optometrist) to determine which combination of individual design parameter values may be most suitable for a given patient. For example, trial kit 500 may be configured to allow the user to employ an iterative optimization process in which the design parameter values are convergent until for the given plurality of trial eye-contact devices 510-1 to 510-n, a combination of device parameters is determined that may be considered optimal for the given patient.

Trial kit 500 may allow a user of trial kit 500 to select at least two of the plurality of trial eye-contact devices 510, and sequentially apply the at least two selected trial eye-contact devices on the same eye of the given patient. The given patient's feedback provided for each one of the at least two selected trial eye-contact devices 510 may be registered (e.g., stored automatically in a computer database). Based on the feedback, the user may select another, trial eye-contact device that possesses design parameters which are, in combination, different from the (first) at least two selected trial eye-contact devices. Based on the patient's feedback in response to trying the other eye-contact device and the at least two selected trial eye-contact devices, the user may select a further other trial eye-contact device. Based on the patient's feedback provided in response to trying the other and the further other trial contact-devices, a yet further other trial contact-device may be selected, and so forth. The user may iteratively proceed with the above noted steps using trial and error to arrive at a combination of device parameters that is optimal for the given user. The procedures outlined herein with respect to trial kit 500 may be performed with the help of slit lamps and/or any other suitable equipment.

It is noted that the term "optimal" as used herein should not be construed in a mathematical limiting manner, as the optimal combination may vary under different circumstances and depend, for example, on environmental factors, on the testing procedures performed, sensitivity of the interpretative faculty of the brain and/or the instruments used in the testing procedure. The expression "determining" used herein in conjunction with procedures for determining the optimal combination, of values relating to device parameters may herein also encompass "heuristically determining", or "using heuristics".

Figure 5A:
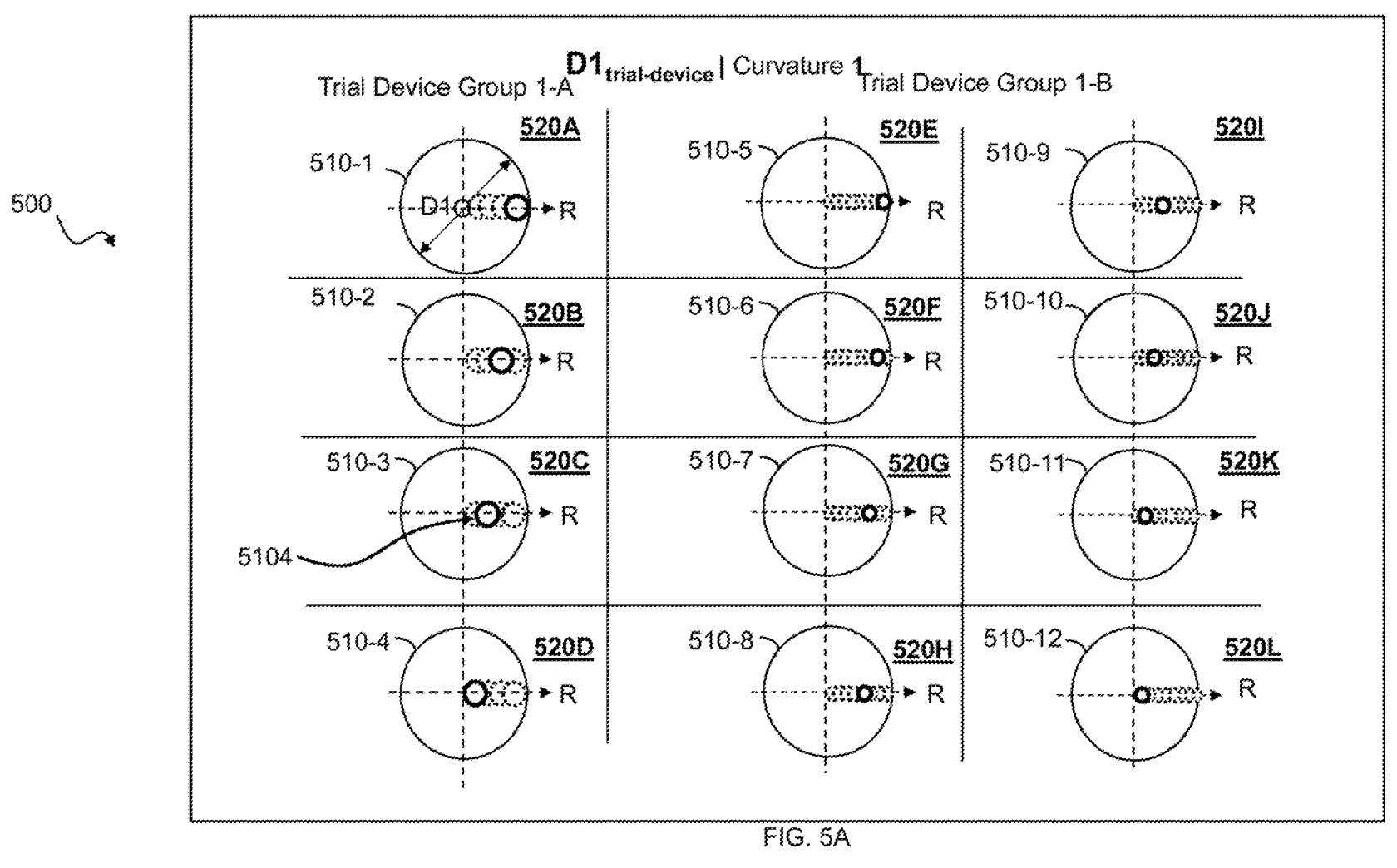
Figure 5B:
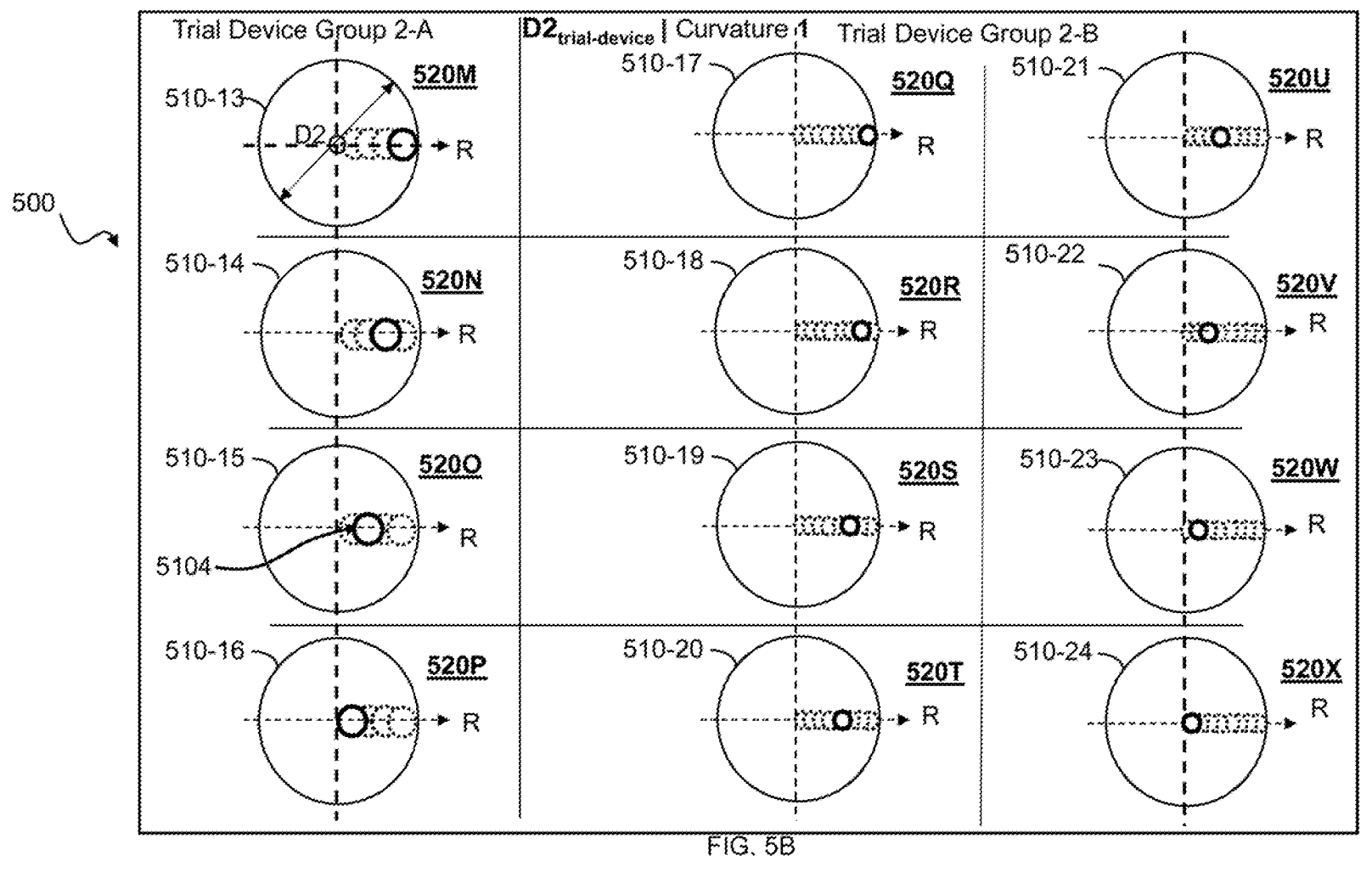

Trial eye-contact devices 510-1 to 510-n may be members of different groups of trial eye-contact devices. Corresponding features are generally indicated by reference numerals increased by 5000. The various groups of trial-contact devices may differ from one another by their device parameters such as, for example, diameter $D_{device}$ and/or by the shape of trial proximal device surface 5103B (e.g., the curvature of concave-shaped proximal surface 5103B). While FIGS. 5A and 5B schematically illustrates a trial set 500 that includes two device groups 1 and 2 which differ from each other by their trial device diameter $D_{trial\text{-}device}$ ($D1_{trial\text{-}device} < D2_{trial\text{-}device}$) only, this should by no means be construed limiting. Optionally, trial kit 500 may comprise more than 2 groups of trial eye-contact devices allowing trial of various combinations of device diameters and shape of proximal device surface 5103B to cover and conformably fit onto the patient's cornea 208. For instance, considering four different diameters and eight different curvatures of proximal device surface 5103B, a trial set 500 may comprise 32 groups of trial eye-contact devices 510.

As schematically shown in FIGS. 5A and 5B, at least one group or each group of trial eye-contact device may comprise one or more subsets of trial devices, exemplified in FIGS. 5A and 5B by the two subsets A and B (e.g., group 1-A and group 1-B). Each subset may be defined by a different sized diameter $d_{transmissive}$ of "trial" light-transmissive portion 5104.

Considering for instance that $D_{device1}=8$ mm and $d_{transmissive}=1$ mm, the first subset A of group 1 may comprise 4 trial devices 510-1 to 510-4 in which trial light-transmissive portion 5104 is respectively shifted from the center of trial devices by 1 mm, 2, mm, 3 mm, and 4 mm from the center (left side of FIG. 5A).

Considering now for example that $D_{device1}=8$ mm and $d_{transmissive}=0.5$ mm, then the second subset B of group 1 may comprise 8 trial devices 510-5 to 510-12 in which for each trial device 510, trial light-transmissive portion 5104 is displaced from the center O of trial device by 0.5 mm, 1 mm, 1.5 mm, 2 mm, 2.5 mm, 3 mm, 3.5 mm, 4 mm from the center. The relative displacement of trial light-transmissive portions 5104 in the different trial devices 510 is schematically indicated by broken circular lines.

Clearly, the configuration or setup of trial kit 500 referred to herein should not be construed in a limiting manner. Accordingly, alternative trial set configurations may be employed.

Optionally, a first trial set may be provided for selecting the device having a suitable diameter and proximal device surface 5103B, and second trial set may be provided for selecting the size and/or orientation of trial light-transmissive portion 5104.

In an embodiment, a trial kit may comprise compartments 520 (e.g., compartments 520A-520X) configured to receive, trial eye-contact devices 510 and indicate information, for example, about device diameter, curvature of trial proximal device surface 5103B, diameter of trial light-transmissive portion 5104 received in respective compartments 520, etc. Optionally, trial kit 500 comprises trial eye-contact devices 510 which are sorted, e.g., in compartments 520, according to the different design parameters of trial eye-contact devices 510.

Optionally, trial kit 500 may comprise various trial eye-contact devices that can allow the user to test various devices to determine which device parameters can at least partially correct or at least partially or fully compensate for refractive errors of eye 200. That is in addition to causing propagation of light 50 via light-transmissive portion 104 to be incident (e.g., focus) onto new main vision spot 203, which is different from macula 205.

Optionally, once the device's diameter $D_{device}$ and curvature of trial proximal device surface 5103B suitable for a given patient has been determined, the user selects of trial set 500 a trial eye-contact devices having a given light transmissive aperture and, additionally, the suitable diameter $D_{device}$ and curvature of trial proximal device surface 5103B. The selected eye-contact devices may be operably positioned on the patient's eye 200 the user and rotated (e.g., by the user) 360 degrees (in clockwise or counterclockwise direction relative to the eye's optical axis $Z_{eye}$). Optionally, during rotation or after a certain degree of rotation has been imparted on the selected trial eye-contact devices by the user (e.g., manually) relative to the patient's cornea 208, the given patient may be asked to gaze at an eye chart and to provide feedback. Based on the provided feedback, his/her visual acuity may be determined for the corresponding rotational position and diameter of light-transmissive portion 104 on his/her eye 200. This procedure may be repeated for a variety of selected trial eye-contact devices, e.g., in an iterative manner, until the parameters for manufacturing a definite eye-contact device possessing optimal parameters for the given patient are determined. Additional or alternative eye-acuity testing systems and/or methods may be employed.

In some embodiments, the procedures and methods outlined herein may be performed to improve a patient's mono-vision capabilities.

In some embodiments, the above procedures may first be accomplished for one of the two eyes of the patient that is comparatively more adversely affected by a medical condition. In some other embodiments, the above procedures may first be accomplished for one of the two eyes of the patient that is comparatively less adversely affected by a medical condition.

In some embodiments, the definite other eye-contact device may be provided or manufactured so that for the same patient, anew left main vision spot 203I and new right main vision spot 203R correspond with each other to allow the patient's brain to construct a single image.

Figure 6:
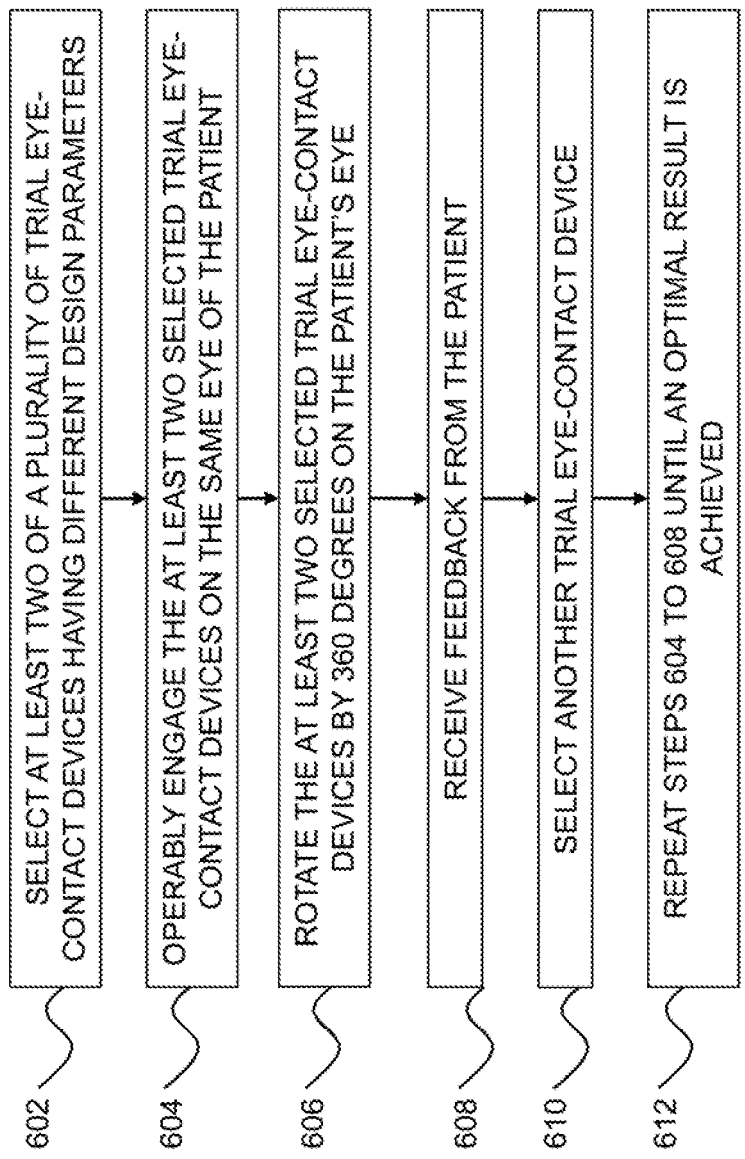
FIG. 6 is a schematic flow chart of a method for obtaining information pertaining to the clinical condition of a patient's eye, according to some embodiments.

Additionally referring to FIG. 6, a method for obtaining information pertaining to the (e.g., clinical) condition of a patient's eye 200 may comprise, for example, selecting at least two of a plurality of trial eye-contact devices. Each one of the at least two selected trial eye-contact devices has different design parameters (step 602).

The method may then further include applying or operably engaging the at least two selected trial eye-contact devices with the same eye 200 of the patient (step 604).

The method including rotating the at least two selected trial eye-contact devices by 360 degrees on the patient's eye (Step 606) and receive a feedback from the patient (step 608).

The method may further include selecting another trial-eye contact device based on the feedback received from the patient (step 610). Optionally, the other trial-eye contact device may have design parameters which differ from the design parameters of any of the trial eye-contact devices selected in preceding steps. Optionally, the other trial-eye contact device may be identical to one of the previously selected trial eye-contact devices. Optionally, the other trial-eye contact device is selected such to improve the patient's acuity and/or comfort.

As indicated by step 612 the method may include repeating steps 604 to 608 until, taking for instance into consideration the patient's feedback and available trial devices, optimal results are obtained, e.g., with respect to visual acuity and/or patient comfort. Additional reference is made to FIGS. 7A-7B. Aspects of some embodiments concern an intraocular implantable device such as an implantable intraocular lens (IOL) or an implantable artificial iris. The intraocular implantable device may have a substantially circular (e.g., disk- or lens-shaped) body having a symmetry axis and comprise a light-transmissive portion and an opaque portion. The light-transmissive portion has an optical axis that is decentered with respect to the symmetry axis. The intraocular implantable device may be fixated within the patient's eye by employing, for example fasteners such as staples, sutures and/or the like.

In some embodiments, an implantable artificial iris (also: artificial iris) 700 which can be used as an intraocular implant and having a having a substantially circular-shaped body may be employed instead or in addition to contact lens body 102.

Artificial iris 700 includes a light-transmissive portion (also: area) 704 and an opaque portion or area 706 that is non-transmissive (also: substantially non-transmissive) to visible light. Optionally, light-transmissive portion 704 and opaque portion 706 complement each other to form artificial iris 700. Artificial iris 700 may be adapted or configured such that when in operable position it is positioned at an orientation relative to the patient's retina 202 such that at least some of light propagating through light-transmissive portion 704 is incident onto new main vision spot 203 of the patient's retina 202 that is not yet or only partially damaged due to AMD and/or other ophthalmic or ocular diseases. Optionally, light which propagated through the eye's cornea may be blocked by opaque portion 706 of artificial iris 700 such that only an unblocked portion thereof herein can propagate towards new main vision spot 203. Light entering the cornea is herein designated by numeric reference "750", light being incident onto the iris is herein designated by numeric reference "752", and light being incident onto new main vision spot 203 is herein designated by numeric reference "754".

Causing a portion of incoming light 750 to be incident onto new main vision spot 203 may improve acuity of patients suffering for instance of AMD or other diseases, e.g., from a category defining a patient as "legally blind" to above the said category, e.g., "functional". Exemplarily, acuity of vision for the respective eye may be increased from 1/60 or 6/60, to 6/24, 6/30, 6/15, or to 6/12. Exemplarily, acuity of vision for the respective can be increased by at least 10%, 20%, 30%, 40%, 50%, 60%, 70%, 80% 90%, 100%, 110%, by at least 120%, by at least 130%, by at least 140%, by at least 150%, by at least 160%, by at least 170%, by at least 180%, by at least 190%, by at least 200%, or by at least 250%, e.g., with respect to a visual acuity determined, e.g., by an eye chart, prior to employing artificial iris 700. In some embodiments, artificial iris 700 may be adapted or configured such that, when in operable position, light is focused onto new main vision spot 203.

Light-transmissive portion 704 may be implemented by a fluid-sealed aperture (also: a physical hole or a pinhole) or physical through-hole extending from distal device surface 703A to proximal device surface 703B of artificial iris 700. Otherwise stated, opaque portion 706 may form a through-hole 704 in artificial iris 110.

Additional reference is made to FIGS. 7C and 7D. It is noted that in the FIGS. 7A-7D the eye's lens is not illustrated merely for simplicity and clarity, and without be construed in a limiting manner.

FIG. 7C schematically illustrates a patient's iris in a "normal" or "non-expanded state". Such non-expanded state may refer to a state of an iris 206 and corresponding size of pupil 207 under normal or "good" lighting conditions, excluding night or other low-light visibility conditions.

FIG. 7C schematically illustrates in conjunction with FIG. 7D that the distance of optical axis $Z_{alt}$ of light-transmissive portion 704 relative to the eye's optical axis Zeye may in some embodiments extend beyond the boundary of pupil 207 when the latter is in the non-expanded state. In other words, distance R1 of the optical axis $Z_{alt}$ of light-transmissive portion 704 may exceed the pupil's radius which would be formed by iris 206 if the iris was present and in the non-expanded state. In some embodiments, artificial iris 700 may be configured to focus light 754 onto new main vision spot 203 that may be located on or at a portion of retina 202 which is different from the vision spot onto which light would be focused if the patient's iris 206 was present instead of implanted artificial iris 700. Optionally, the new main vision spot may be within the macula but outside the fovea, Optionally, the new main vision spot may be outside the patient's macula.

Various techniques may be employed to widen the diameter of light-transmissive portion of an implantable ophthalmic device (e.g., an artificial iris or an IOL) including, for example, laser-based techniques which may optionally employ eye-safe lasers, In some embodiments, a trial set and method may be employed to iteratively arrive at design parameter values such that the implantable ophthalmic device is custom-fitted to a given patient. Such example trial set and method is described herein with respect to FIGS. 4-6. In some embodiments, trial eye-contact devices may be employed to arrive at design parameter values for an artificial iris for example. Optionally, the distance between the artificial iris when implanted and the position of the trial eye-contact devices may be taken into account to offset for errors in the optical path.

Similar to what has been outlined herein with artificial iris 700, an IOL (not shown) may be configured to have a light-transmissive and an opaque portion to focus light onto a new main vision spot.

Unless otherwise stated, the use of the expression "and/or" between the last two members of a list of options for selection indicates that a selection of one or more of the listed options is appropriate and may be made.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable subcombination or as suitable in any other described embodiment, example or option of the invention. Certain features described in the context of various embodiments, examples and/or options are not to be considered essential features of those embodiments, unless the embodiment, example and/or option is inoperative without those elements.

It is noted that the term "exemplary" is used herein to refer to examples of embodiments and/or implementations, and is not meant to necessarily convey a more-desirable use-case.

The number of elements shown in the Figures should by no means be construed as limiting and is for illustrative purposes only.

While the invention has been described with respect to a limited number of embodiments, these should not be construed as limitations on the scope of the invention, but rather as exemplifications of some of the embodiments.

As used herein, unless otherwise specified, the use of the ordinal adjectives "first", "second" etc., to describe like objects, merely indicate that different instances of like objects are being referred to, and are not intended to imply that the objects so described must be in a given sequence, temporally, in ranking, and/or in any other manner.

It should be understood that where the claims or specification refer to "a" or "an" element and/or feature, such reference is not to be construed as there being only one of that element. Hence, reference to "an element" or "at least one element" for instance may also encompass "one or more elements".

The terms "substantially," and the like refer to, considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein. For example, the terms "substantially" and/or "about" with respect to a magnitude or a numerical value may imply to be within an inclusive range of −10% to +10% of the respective magnitude or value.

It should be noted that the term "light" or "visible light" as used herein may refer to electromagnetic radiation of any suitable wavelength for the purposes of the applications disclosed herein. For example, the term "light" may include a wavelength range of electromagnetic radiation that can be seen by a healthy visual system of humans or other mammals.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

While the invention has been described with respect to a limited number of embodiments, these should not be construed as limitations on the scope of the invention, but rather as exemplifications of some of the embodiments.

What is claimed is:

1. An implantable intraocular lens (IOL) comprising:
a substantially circular-shaped intraocular lens body implantable behind a cornea of an eye of a patient and having a rotational symmetry axis that virtually intersects a location on a retina lying within a radius of a non-dilated pupil,
the substantially circular-shaped intraocular lens body having an anterior surface and a posterior surface, comprising:
an opaque portion that is non-transmissive to visible light; and
a light-transmissive portion consisting of a single pinhole that is decentered in its entirety with respect to the rotational symmetry axis of the substantially circular-shaped intraocular lens body such that, when the circular-shaped intraocular lens body is operably engaged with a patient's eye, the optical axis of the pupil is entirely outside the pinhole, said pinhole is operable to direct light from the anterior surface to the posterior surface along an optical axis that is different from the symmetry axis of the substantially circular-shaped intraocular lens body,
wherein the optical axis of the single pinhole intersects a second location of the retina exceeding the radius of the non-dilated pupil,
wherein substantially the entirety of the intraocular lens body is comprised by the opaque portion,
wherein when the substantially circular-shaped intraocular lens body operably engages with a patient's eye, the rotational symmetry axis coincides with the optical axis of the eye, and
further wherein the intraocular lens body is configured to direct light propagating through the light-transmissive portion such to be incident onto the second location that is within the eye's macula but not on the fovea located in the macula.

2. The intraocular lens of claim 1, wherein the substantially circular-shaped intraocular lens body is disk-shaped or lens-shaped.

3. The intraocular lens of claim 1, wherein the light-transmissive portion is a physical through-hole that extends from the anterior surface to the posterior surface of the substantially circular-shaped intraocular lens body.

4. The lens of claim 1, wherein the substantially circular-shaped body is operable to at least partially or fully compensate for optical errors of the patient's eye.

5. The intraocular lens of claim 4, wherein the substantially circular-shaped body is operable to at least partially compensate for myopia, hyperopia and/or astigmatism of the patient's eye.

6. The intraocular lens of claim 1, wherein said light-transmissive portion comprises a distal end and a proximal end, further wherein said distal end and said proximal end are shaped in a biconcave or biconvex manner.

* * * * *